US00PP27240P2

(12) United States Plant Patent
Zuikevich

(10) Patent No.: US PP27,240 P2
(45) Date of Patent: Oct. 4, 2016

(54) ***BRUNNERA* PLANT NAMED 'SILVER CHARM'**

(50) Latin Name: *Brunnera macrophylla*
Varietal Denomination: Silver Charm

(71) Applicant: Alexander Zuikevich, Minsk (BY)

(72) Inventor: Alexander Zuikevich, Minsk (BY)

( * ) Notice: Subject to any disclaimer, the term of this patent is extended or adjusted under 35 U.S.C. 154(b) by 0 days.

(21) Appl. No.: 14/545,804

(22) Filed: Jun. 22, 2015

(51) Int. Cl.
*A01H 5/02* (2006.01)

(52) U.S. Cl.
USPC ..... Plt./412

(58) Field of Classification Search
USPC ..... Plt./412
CPC ..... A01H 5/02
See application file for complete search history.

*Primary Examiner* — Kent L Bell
(74) *Attorney, Agent, or Firm* — Klarquist Sparkman, LLP

(57) ABSTRACT

A new and distinct form of *Brunnera macrophylla* characterized by heart-shaped, green leaves with a strong silver white veil and green veins, short stems of sky blue flowers, a fast growing, dense compact habit that forms many crowns quickly and grows to a medium size plant, and excellent vigor.

1 Drawing Sheet

Botanical denomination: *Brunnera macrophylla.*
Variety designation: 'Silver Charm'.

BACKGROUND OF THE INVENTION

The present invention relates to a new and distinct cultivar of *Brunnera macrophylla*, given the name, 'Silver Charm'. *Brunnera* is in the family Boraginaceae. This new cultivar was found in a private garden in Minsk, Belarus.

This plant exhibits the following characteristics that make it unique:

1. heart-shaped, green leaves with a strong silver white veil and green veins,
2. short stems of sky blue flowers,
3. a fast growing, dense compact habit that forms many crowns quickly and grows to a medium size plant, and
4. excellent vigor.

This plant is unique in its combination of intense silver veiling of the leaves and the very large leaf and plant size.

Compared to *Brunnera* 'Jack Frost' (U.S. Plant Pat. No. 13,859), the new cultivar is faster growing and forms more crowns faster. The new cultivar has a smaller leaf that is usually narrower and more heart-shaped rather than saggitate.

Compared to *Brunnera* 'Langtrees', an unpatented plant, the new cultivar has a stronger and larger white veil over the leaf and leaves that are narrower and more heart-shaped rather than saggitate.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an 18-month-old *Brunnera* 'Silver Charm' growing in the field in flower in late March in Canby, Oreg.

FIG. 2 shows a 9-month-old *Brunnera* 'Silver Charm' growing in the field in summer in Canby, Oreg.

DETAILED PLANT DESCRIPTION

The following is a detailed description of the new *Brunnera* cultivar based on observations of two-year-old specimens in flower grown growing outside in the field trials in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form.*—Rhizomatous, herbaceous perennial.
*Cold hardiness.*—USDA Zone 3-8.
*Size.*—Grows to 31 cm wide and 20 cm high.
*Stem.*—Rosette.
*Vigor.*—Excellent.

Leaf:

*Type.*—Simple.
*Arrangement.*—Basal.
*Shape.*—Cordate to broadly ovate.
*Venation.*—Pinnate, Green 137B on top and Yellow Green 147C on the bottom side.
*Margins.*—Entire, slightly undulate.
*Apex.*—Acuminate.
*Base.*—Cordate.
*Blade size.*—Grows to 11 cm long and 9 cm wide.
*Surface texture.*—Coarsely pubescent on both sides.
*Petiole description.*—Grows to 18.5 cm long and 5 mm wide, coarsely pubescent, Yellow Green 147C darkening to Greyed Purple 187A at base.
*Leaf color.*—Topside Green 137B on margins and veins with white interveinally, White NN155C, bottom side between Green 137B and 138B.

Inflorescence:

*Type.*—Terminal panicle.
*Number of flowers.*—About 100 to 150 per panicle.

*Peduncle*.—Grows 16 cm to 27 cm tall and 4 mm wide, pubescent, closest to Yellow Green 155C tinted Greyed Purple 187A, with about 9 to 11 small petiolate to sessile leaves (grows to 40 mm long and 1.6 mm wide, ovate, entire and slightly undulate, tip acute, base truncate to attenuate, pubescent on both sides, topside Green 137B with slight interveinal silvering, White NN155C, bottom side between Green 137B and 138B).

*Pedicel*.—2 mm long, less than 1 mm wide, pubescent, Yellow Green 144A tinted Greyed Purple 187A in high light.

*Bloom period*.—April to June in Canby, Oreg.

Flower bud:

*Size*.—2 mm wide and 3 mm deep.

*Description*.—Orbicular.

*Surface texture*.—Glabrous.

*Color*.—Violet Purple 91A.

Flower:

*Type*.—Regular.

*Shape*.—Rotate.

*Corolla description*.—7 mm wide and 2 mm deep, top side colored Blue 101B with a White NN155C eye, bottom side Blue 100C; with 5 obovate lobes, each 2 mm wide and 2 mm deep, margin entire, tip obtuse, base attenuate, glabrous on both sides, tube 1 mm long and 1 mm wide, Blue 100D outside.

*Calyx description*.—Campanulate, 1 mm wide and 1.5 mm deep, 5-lobed, lobes cut to ⅔ down, ovate, acute, entire, pubescent outside, glabrous inside, Yellow Green 144A.

*Pistil description*.—1, 1 mm long, Yellow Green 144A, ovary 4 lobed and about 0.5 mm long, style and stigma 0.5 mm long.

*Stamen description*.—5, filaments 1 mm long and White 155D, anthers 1 mm long and Black 202A, pollen White 155A.

*Fragrance*.—None.

*Lastingness*.—A spike blooms for about 3 weeks on the plant.

Seed: Nutlets, round, less than 1 mm in size, Brown 200A.

Pests and diseases: 'Silver Charm' no major pests or disease problems.

I claim:

1. A new and distinct *Brunnera* plant substantially as illustrated and described.

* * * * *

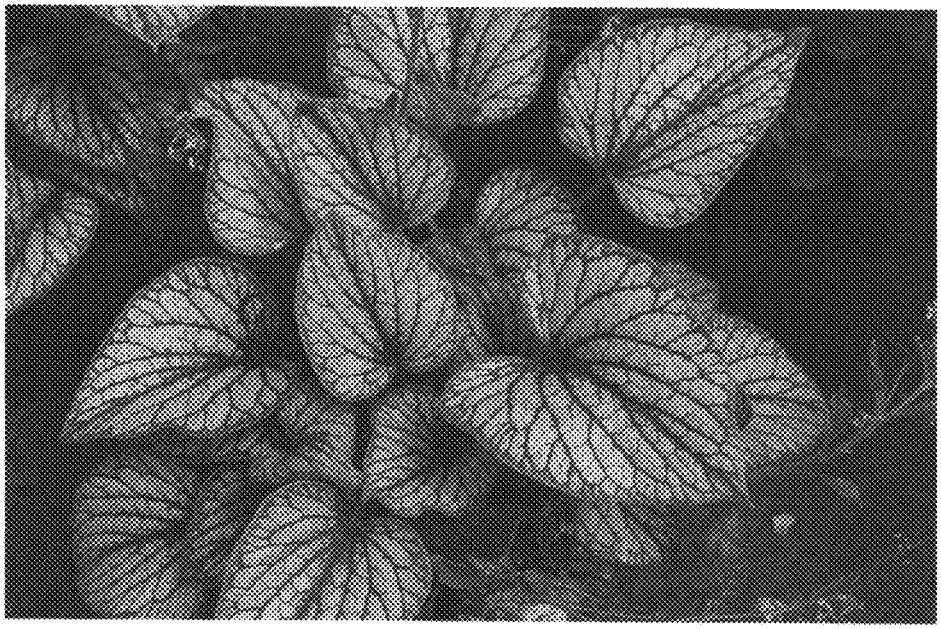

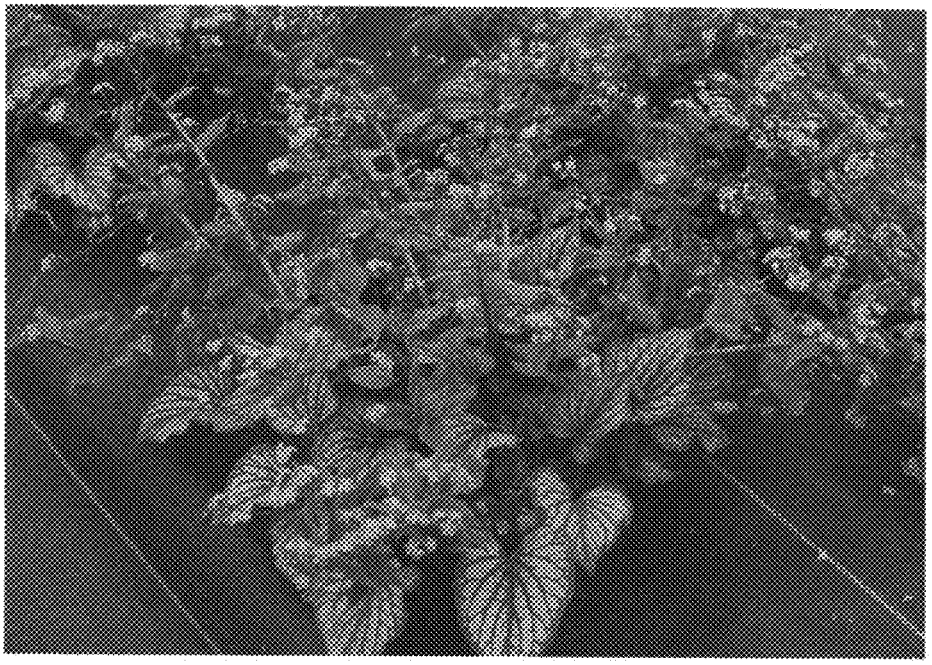
FIG. 1 above, FIG. 2 below